(12) United States Patent
Mastroianni et al.

(10) Patent No.: US 8,546,589 B2
(45) Date of Patent: Oct. 1, 2013

(54) ORGANOPHOSPHORUS COMPOUNDS, CATALYTIC SYSTEMS COMPRISING SAID COMPOUNDS AND METHOD OF HYDROCYANATION USING SAID CATALYTIC SYSTEMS

(75) Inventors: Sergio Mastroianni, Lyons (FR); Paul Pringle, Bristol (GB); Ana Maldonado, Gradignan (FR); Gad Rothenberg, Oegstgeest (NL); Igor Mikhel, Moscow (RU)

(73) Assignee: Rhodia Operations, Aubervilliers (FR)

( * ) Notice: Subject to any disclaimer, the term of this patent is extended or adjusted under 35 U.S.C. 154(b) by 0 days.

(21) Appl. No.: 13/497,016

(22) PCT Filed: Aug. 31, 2010

(86) PCT No.: PCT/EP2010/062755
§ 371 (c)(1),
(2), (4) Date: Sep. 4, 2012

(87) PCT Pub. No.: WO2011/032835
PCT Pub. Date: Mar. 24, 2011

(65) Prior Publication Data
US 2013/0053580 A1 Feb. 28, 2013

(30) Foreign Application Priority Data

Sep. 18, 2009 (FR) ..................... 09 56428

(51) Int. Cl.
C07F 19/00 (2006.01)
C07F 9/6574 (2006.01)
C07C 253/10 (2006.01)

(52) U.S. Cl.
USPC ........................... 549/212; 549/216; 558/308

(58) Field of Classification Search
None
See application file for complete search history.

(56) References Cited

FOREIGN PATENT DOCUMENTS
WO 2004/103948 12/2004

OTHER PUBLICATIONS

Horiuchiu et al., "(R,S)-BINAPHOS-Ni(O) and -Pd(O) complexes: characterization and use for asymmetric hydrocyanation of norbornene", Tetrahedron: Asymmetry, 1997, pp. 57-63, vol. 8, No. 1, Elsevier Science Ltd., Great Britain.
Hopewell, "New Directions in Phospha-adamantane Chemistry", University of Bristol, Aug. 2009, XP008127653.
International Search Report dated Feb. 16, 2011 in related PCT Application No. PCT/EP2010/062755 filed Aug. 31, 2010, 3 pages.

*Primary Examiner* — Sun Jae Loewe
(74) *Attorney, Agent, or Firm* — Dentons US LLP

(57) ABSTRACT

Organophosphorus compounds are described that belong to the phosphinite-phosphite family. Catalytic systems comprising a metallic element forming a complex with said phosphinite-phosphite compounds and methods of hydrocyanation employed in the presence of said catalytic systems are also described.

20 Claims, No Drawings

ORGANOPHOSPHORUS COMPOUNDS, CATALYTIC SYSTEMS COMPRISING SAID COMPOUNDS AND METHOD OF HYDROCYANATION USING SAID CATALYTIC SYSTEMS

CROSS REFERENCE TO RELATED APPLICATIONS

The present application is the United States national stage of PCT International Application No. PCT/EP2010/62755 filed 31 Aug. 2010, which claims the benefit of French Application No. 0956428 filed 18 Sep. 2009; all of which are incorporated herein by reference in their entireties.

The present invention relates to organophosphorus compounds belonging to the phosphinite-phosphite family, their use in catalytic systems and methods of synthesis of organic compounds using said catalytic systems, notably the methods of hydrocyanation of ethylenically unsaturated organic compounds to compounds comprising at least one nitrile function.

The reaction of hydrocyanation is, for example, described in French patent 1 599 761 which relates to a method of preparation of nitriles by addition of hydrocyanic acid to organic compounds having at least one ethylenic double bond, in the presence of a catalyst comprising nickel and an organophosphorus ligand, a triarylphosphite. This reaction can be carried out in the presence or absence of a solvent.

When a solvent is used, it is preferably a hydrocarbon, such as benzene or xylenes or a nitrile such as acetonitrile.

The catalyst employed is an organic nickel complex, containing ligands such as phosphines, arsines, stibines, phosphites, arsenites or antimonites.

The presence of a promoter for activating the catalyst, such as a boron compound or a metal salt, generally a Lewis acid, is also recommended in said patent.

Numerous other catalytic systems have been proposed, generally comprising organophosphorus compounds belonging to the family of the phosphites, phosphonites, phosphinites and phosphines. These organophosphorus compounds can comprise one phosphorus atom per molecule and are described as monodentate ligands, or several phosphorus atoms per molecule, which are then called multidentate ligands. More particularly, numerous ligands containing two phosphorus atoms per molecule (bidentate ligand) have been described in numerous patents.

However, new catalytic systems with better performance both with respect to catalytic activity and with respect to stability are always being sought for improving the general economics of the method.

One of the aims of the present invention is to propose a novel family of ligands which makes it possible to obtain, with transition metals, catalytic systems displaying good catalytic activity notably in the reactions of hydrocyanation.

For this purpose, the present invention proposes organophosphorus compounds belonging to the phosphinite-phosphite family, said organophosphorus compounds corresponding to one of the general formulae (I) and (II):

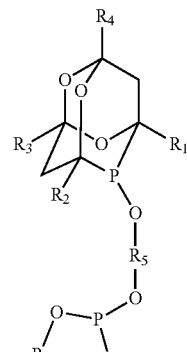
(I)

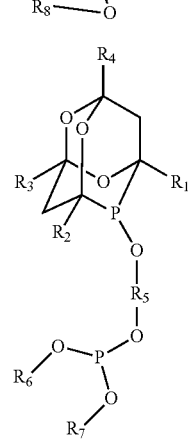
(II)

in which:
$R_1$, $R_2$, $R_3$, $R_4$, $R_6$ and $R_7$, which may be identical or different, represent a hydrogen atom, a linear or branched alkyl radical having from 1 to 12 carbon atoms which can contain heteroatoms, a radical comprising a substituted or unsubstituted aromatic or cycloaliphatic ring which can comprise heteroatoms, a carbonyl, alkoxycarbonyl or alkoxy radical, a halogen atom, a nitrile group or a haloalkyl group having 1 to 12 carbon atoms $R_5$ and $R_8$, which may be identical or different, represent a linear or branched aliphatic radical having from 1 to 12 carbon atoms which can contain heteroatoms, a radical comprising a substituted or unsubstituted aromatic or cycloaliphatic ring which can comprise heteroatoms or several aromatic rings, condensed or joined together.

As preferred compounds of general formulae (I) or (II) of the invention, we may mention the compounds of the following formulae:

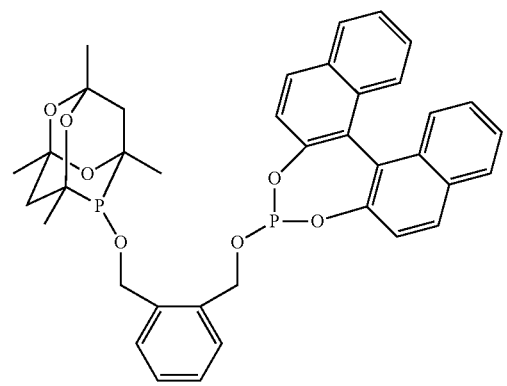

Ligand A

-continued

Ligand B

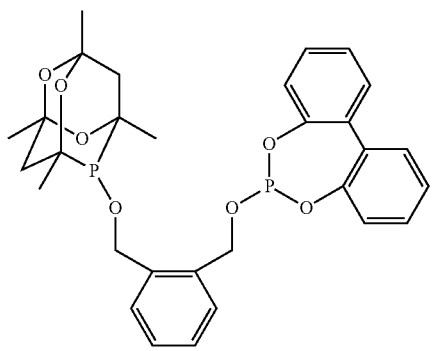

Ligand C

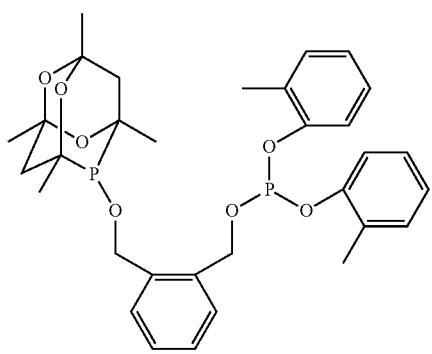

Ligand D

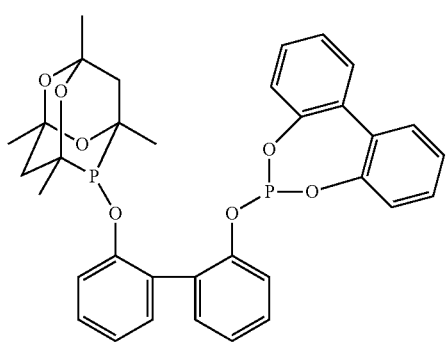

Ligand E

-continued

Ligand F

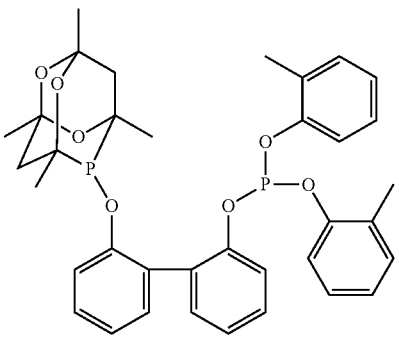

The present invention also proposes a method for preparing these compounds, according to which a compound obtained by reaction of the compound of formula OH—$R_5$—OH with an organoalkali metal compound is reacted, on the one hand, with a CgPX compound of formula (1) below where X represents a halogen atom and, on the other hand, with a halogenated organophosphite corresponding to the phosphite residue linked to R5 in general formulae I and II, of formula (2) or (3)

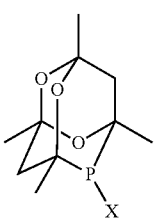 (1)

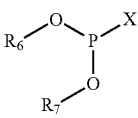 (2)

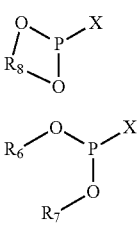 (3)

Advantageously, the compound obtained by reaction of the compound of formula OH—$R_5$—OH with an organoalkali metal compound is reacted with a CgPX compound of formula (1) in a first stage, and then the product of reaction with the halogenated organophosphite corresponding to the phosphite residue linked to R5 in general formulae I and II, of formula (2) or (3), is reacted in a second stage.

Specifically, the compounds of the invention can be prepared from compounds called hereinafter CgPH of the following formula:

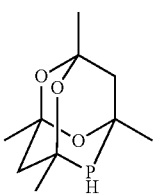

These CgPH compounds are described in the scientific article published in the journal ORGANOMETALLICS Vol. 27, No. 13 p. 3215-3224 of 2008: "General Routes to Alkyl Phosphotrioadamantane Ligands" by Joanne H. Downing et al., as well as their method of synthesis.

The CgPH compounds are transformed to CgPX compounds, in which X represents a halogen atom, preferably bromine, by reaction with the molecular halogen in an organic solvent such as dichloromethane.

The CgPX compounds can then be reacted with a compound obtained by reaction of a hydroxylated compound corresponding to the residue R5 in general formulae I and II with an organoalkali metal compound, preferably organolithium compound, in a solvent such as tetrahydrofuran.

The resulting compound can then be reacted with a halogenated organophosphite corresponding to the phosphite residue linked to R5 in general formulae I and II, preferably a chlorophosphite.

Details and additional information on the methods of manufacture of the compounds of formulae I and II will be given in the examples presented below.

According to another object of the invention, the organophosphorus compounds of formulae (I) or (II) are used for the manufacture of catalytic systems by combining with a metallic element to form a complex. Overall, the composition of these catalytic systems can be represented by general formula (III) (this formula does not correspond to the structure of the compounds and complexes present in the catalytic system):

$$M\,[L_f]_t \tag{III}$$

in which:
M is a transition metal
$L_f$ represents at least one organophosphorus ligand of formula (I) or (II)
t represents a number between 1 and 10 (inclusive).

The metals M that can be complexed are in general all the transition metals of groups 1b, 2b, 3b, 4b, 5b, 6b, 7b and 8 of the periodic system, such as published in "Handbook of Chemistry and Physics, 51st Edition (1970-1971)" by The Chemical Rubber Company.

Among these metals, we may mention more particularly the metals that can be used as catalysts in the reactions of hydrocyanation. Thus, we may mention, as non-limiting examples, nickel, cobalt, iron, ruthenium, rhodium, palladium, osmium, iridium, platinum, copper, silver, gold, zinc, cadmium, mercury. Nickel is the preferred element for the hydrocyanation of olefins and unsaturated nitriles.

The preparation of the catalytic systems comprising compounds of general formula (I) or (II) can be carried out by bringing a solution of a compound of the metal selected, for example nickel, in contact with a solution of the organophosphorus compound of the invention.

The compound of the metal can be dissolved in a solvent. In the compound employed, the metal can be either at the degree of oxidation that it will have in the organometallic complex, or at a higher degree of oxidation.

As an example, it may be mentioned that in the organometallic complexes of the invention, rhodium is at degree of oxidation (I), ruthenium at degree of oxidation (II), platinum at degree of oxidation (0), palladium at degree of oxidation (0), osmium at degree of oxidation (II), iridium at degree of oxidation (I), nickel at degree of oxidation (0).

If, during preparation of the organometallic complex, the metal is employed at a higher degree of oxidation, it can be reduced in situ.

Among the compounds of metals M that can be used for preparing the organometallic complexes, notably when the metal is nickel, we may mention, as non-limiting examples, the following nickel compounds:

compounds in which nickel is at degree of oxidation zero, such as potassium tetracyanonickelate $K_4[Ni(CN)_4]$, nickel zero bis (acrylonitrile), nickel bis (cyclooctadiene-1,5) (also called $Ni(cod)_2$) and derivatives containing ligands such as tetrakis (triphenyl phosphine) nickel zero.

nickel compounds such as carboxylates (notably acetate), carbonate, bicarbonate, borate, bromide, chloride, citrate, thiocyanate, cyanide, formate, hydroxide, hydrophosphite, phosphite, phosphate and derivatives, iodide, nitrate, sulphate, sulphite, aryl- and alkyl-sulphonates.

When the nickel compound used corresponds to an oxidation state of the nickel greater than 0, a reducing agent of the nickel is added to the reaction mixture, preferably reacting with it in the conditions of the reaction. This reducing agent can be organic or mineral. We may mention, as non-limiting examples, the borohydrides such as $BH_4Na$, $BH_4K$, Zn powder, magnesium or hydrogen.

When the nickel compound used corresponds to oxidation state 0 of the nickel, it is also possible to add a reducing agent such as those mentioned above, but said addition is not imperative.

When an iron compound is used, the same reducing agents are suitable. In the case of palladium, the reducing agent can be, additionally, elements of the reaction mixture (solvent, olefin).

The present invention also relates to a method of hydrocyanation of olefins, more particularly of diolefins for the manufacture of nitrile compounds, more particularly of dinitrile compounds.

The organic compounds bearing at least one ethylenic double bond more particularly employed in the present method are diolefins such as butadiene, isoprene, hexadiene-1,5, cyclooctadiene-1,5, ethylenically unsaturated aliphatic nitriles, particularly the linear pentene-nitriles such as pentene-3-nitrile, pentene-4-nitrile as well as monoolefins such as styrene, methylstyrene, vinylnaphthalene, cyclohexene, methylcyclohexene as well as mixtures of several of these compounds.

The pentene-nitriles can contain, in addition to pentene-3-nitrile and pentene-4-nitrile, amounts, generally minor, of other compounds, such as methyl-2-butene-3-nitrile, methyl-2-butene-2-nitrile, pentene-2-nitrile, valeronitrile, adiponitrile, methyl-2-glutaronitrile, ethyl-2-succinonitrile or butadiene, resulting for example from the previous reaction of hydrocyanation of butadiene to unsaturated nitriles.

In fact, during the hydrocyanation of butadiene, there is formation, along with the linear pentene-nitriles, of non-negligible amounts of methyl-2-butene-3-nitrile and methyl-2-butene-2-nitrile.

The catalytic system used for the hydrocyanation according to the method of the invention can be prepared before it is fed into the reaction zone, for example by adding to the compound of formula (I), (II), (III) or (IV), alone or dissolved in a solvent, the appropriate amount of the selected transition metal compound and optionally of the reducing agent. It is also possible to prepare the catalytic system "in situ" simply by adding the compound of formula (I), (II), (III) or (IV) and the transition metal compound to the hydrocyanation reaction mixture before or after adding the compound that is to undergo hydrocyanation.

The amount of compound of nickel or of another transition metal used is selected to obtain a concentration in mol of transition metal per mol of organic compounds to undergo hydrocyanation or isomerization between $10^{-4}$ and 1, and preferably between 0.005 and 0.5 mol of nickel or of the other transition metal employed.

The amount of compound of formula (I) or (II) used to form the catalyst is selected in such a way that the number of moles of this compound relative to 1 mol of transition metal is from 0.5 to 100 and preferably from 0.5 to 50.

Although the reaction is generally carried out without solvent, it may be advantageous to add an inert organic solvent. The solvent can be a solvent of the catalyst which is miscible with the phase comprising the compound that is to undergo hydrocyanation at the temperature of hydrocyanation. As examples of such solvents, we may mention aromatic, aliphatic or cycloaliphatic hydrocarbons.

The hydrocyanation reaction is generally carried out at a temperature from 10° C. to 200° C. and preferably from 30° C. to 120° C. It can be carried out in a single-phase medium.

The method of hydrocyanation of the invention can be used continuously or discontinuously.

The hydrogen cyanide employed can be prepared from metal cyanides, notably sodium cyanide, or from cyanohydrins, such as acetone cyanohydrin or by any other known method of synthesis such as Andrussov's method consisting of reacting methane with ammonia and air.

Anhydrous hydrogen cyanide is fed into the reactor in the form of gas or liquid. It can also be dissolved beforehand in an organic solvent.

For discontinuous (batch) application, in practice a reactor, previously purged with an inert gas (such as nitrogen, argon), is charged either with a solution containing some or all of the various constituents such as the compound of formula I or II, the transition metal (nickel) compound, the optional reducing agent and solvent, or with said constituents separately. Generally the reactor is then heated to the selected temperature, and then the compound that is to undergo hydrocyanation is introduced. The hydrogen cyanide itself is then introduced, preferably continuously and evenly.

When the reaction (the progress of which can be monitored by assaying samples) is completed, the reaction mixture is withdrawn after cooling and the reaction products are isolated and separated, for example by distillation.

Advantageously, the synthesis of dinitriles such as adiponitrile from diolefins (butadiene) is conducted in two successive stages. The first stage consists of hydrocyanation of a double bond of the diolefin to obtain an unsaturated mononitrile. The second stage consists of hydrocyanation of the unsaturation of the mononitrile to obtain the corresponding dinitrile or dinitriles. These two stages are generally implemented with a catalytic system comprising an organometallic complex of the same nature. However, the organophosphorus compound/metallic element ratios and the concentration of catalyst can be different. Moreover, it is preferable to combine the catalytic system with a cocatalyst or promoter in the second stage. This cocatalyst or promoter is generally a Lewis acid.

The Lewis acid used as cocatalyst notably makes it possible, in the case of hydrocyanation of ethylenically unsaturated aliphatic nitriles, to improve the linearity of the dinitriles obtained, i.e. the percentage of linear dinitrile relative to all of the dinitriles formed, and/or to increase the activity and the working life of the catalyst.

Lewis acid means, in the present text, according to the usual definition, compounds that are acceptors of electron doublets.

It is notably possible to use the Lewis acids mentioned in the work published by G. A. OLAH "Friedel-Crafts and related Reactions", Vol. I, pages 191 to 197 (1963).

The Lewis acids that can be employed as cocatalysts in the present method are selected from the compounds of the elements of groups Ib, IIb, IIIa, IIIb, IVa, IVb, Va, Vb, VIb, VIIb and VIII of the periodic system. Most often these compounds are salts, notably halides, such as chlorides or bromides, sulphates, sulphonates, halosulphonates, perhaloalkyl sulphonates, notably fluoroalkylsulphonates or perfluoroalkylsulphonates, carboxylates and phosphates.

As non-limiting examples of said Lewis acids, we may mention zinc chloride, zinc bromide, zinc iodide, manganese chloride, manganese bromide, cadmium chloride, cadmium bromide, stannous chloride, stannous bromide, stannous sulphate, stannous tartrate, indium trifluoromethylsulphonate, chlorides or bromides of rare earth elements such as lanthanum, cerium, praseodymium, neodymium, samarium, europium, gadolinium, terbium, dysprosium, hafnium, erbium, thallium, ytterbium and lutetium, cobalt chloride, ferrous chloride, yttrium chloride.

It is also possible to use organometallic compounds as Lewis acid, such as triphenylborane, titanium isopropylate or the compounds described in French patent application FR 2926816.

It is of course possible to use mixtures of several Lewis acids.

Among the Lewis acids, zinc chloride, zinc bromide, stannous chloride, stannous bromide, triphenylborane and zinc chloride/stannous chloride mixtures are quite particularly preferred.

The Lewis acid cocatalyst employed generally represents from 0.01 to 50 mol per mol of transition metal compound, more particularly of nickel compound, and preferably from 1 to 10 mol per mol.

The unsaturated mononitriles employed in this second stage are advantageously linear pentene-nitriles such as pentene-3-nitrile, pentene-4-nitrile and mixtures thereof.

These pentene-nitriles can contain amounts, generally minor, of other compounds, such as methyl-2-butene-3-nitrile, methyl-2-butene-2-nitrile, pentene-2-nitrile.

The catalytic solution used for hydrocyanation in the presence of Lewis acid can be prepared before it is fed into the reaction zone, for example by adding, to the compound of formula (I) or (II), the appropriate amount of transition metal compound selected, of Lewis acid and optionally of reducing agent. It is also possible to prepare the catalytic solution "in situ" simply by adding these various constituents to the reaction mixture.

It is also possible, in the conditions of the method of hydrocyanation of the present invention, and notably by working in the presence of the catalytic system described previously comprising a compound of formula (I) or (II) and at least one compound of a transition metal, to carry out, in the absence of hydrogen cyanide, the isomerization of methyl-2-butene-3-nitrile to pentenenitriles, and more generally of the branched unsaturated nitriles to linear unsaturated nitriles.

The methyl-2-butene-3-nitrile submitted to isomerization according to the invention can be employed alone or mixed with other compounds. Thus, it is possible to use methyl-2-butene-3-nitrile mixed with methyl-2-butene-2-nitrile, pentene-4-nitrile, pentene-3-nitrile, pentene-2-nitrile, butadiene.

It is particularly advantageous to treat the reaction mixture resulting from hydrocyanation of butadiene with HCN in the presence of at least one compound of formula (I) or (II) and of at least one compound of a transition metal, more preferably a nickel compound with degree of oxidation 0, as defined previously. Within the scope of this preferred variant, as the catalytic system is already present for the reaction of hydrocyanation of butadiene, it is sufficient to stop all feed of hydrogen cyanide, to allow the isomerization reaction to take place.

In this variant it is possible, if necessary, to carry out a light purge of the reactor with an inert gas such as nitrogen or argon for example, in order to expel any hydrocyanic acid that might still be present.

The isomerization reaction is generally carried out at a temperature between 10° C. and 200° C. and preferably between 60° C. and 140° C.

In the preferred case of isomerization immediately following the reaction of hydrocyanation of butadiene, it will be advantageous to work at the temperature at which the hydrocyanation was carried out or slightly higher.

Just as for the method of hydrocyanation of ethylenically unsaturated compounds, the catalytic system used for isomerization can be prepared before it is fed into the reaction zone, for example by mixing the compound of formula (I) or (II), with the appropriate amount of transition metal compound selected and optionally of reducing agent. It is also possible to prepare the catalytic system "in situ" simply by adding these various constituents to the reaction mixture. The amount of transition metal compound and more particularly of nickel used, as well as the amount of compound of formula (I) or (II), are the same as for the reaction of hydrocyanation.

Although the isomerization reaction is generally carried out without solvent, it may be advantageous to add an inert organic solvent, which can be used subsequently as extractant. This is notably the case when such a solvent was employed in the reaction of hydrocyanation of butadiene, having been used for preparing the medium submitted to the isomerization reaction. Said solvents can be selected from those mentioned previously for hydrocyanation.

However, the preparation of dinitrile compounds by hydrocyanation of an olefin such as butadiene can be carried out using a catalytic system according to the invention for the stages of formation of the unsaturated nitriles and the aforementioned stage of isomerization, and the reaction of hydrocyanation of the unsaturated nitriles to dinitriles can be carried out with a catalytic system according to the invention or any other catalytic system already known for this reaction.

Similarly, the reaction of hydrocyanation of the olefin to unsaturated nitriles and the isomerization of the latter can be carried out with a catalytic system different from that of the invention, the stage of hydrocyanation of the unsaturated nitriles to dinitriles being carried out with a catalytic system according to the invention.

Other details and advantages of the invention will be illustrated by the examples given below, which are purely for illustration and are non-limiting.

EXAMPLES

Abbreviations Used
Ph: phenyl radical
Cod: cyclooctadiene
$Ni(Cod)_2$: bis(1,5-cyclooctadiene)nickel
3PN: 3-pentenenitrile
AdN: adiponitrile
ESN: ethylsuccinonitrile
MGN: methylglutaronitrile
DN: dinitrile compounds (AdN, MGN or ESN)
TIBAO: tetraisobutyldialuminoxane
RR(DN): true yield of dinitriles corresponding to the ratio of the number of moles of dinitriles formed to the number of moles of 3PN used Linearity (L): ratio of the number of moles of AdN formed to the number of moles of dinitriles formed (sum of the moles of AdN, ESN and MGN)

The following compounds: 3PN, $Ni(Cod)_2$, $ZnCl_2$, TIBAO, $BPh_3$, diphenylborinic anhydride ($Ph_2BOPh_2$) are known products and are commercially available.

Examples 1 to 3

Preparation of Ligands A to C

In a first stage, a solution of $Br_2$ (3.5158 g, 0.022 mol) in $CH_2Cl_2$ (30 ml) is added in 30 minutes to a solution of CgPH (4.3243 g, 0.02 mol) in 60 ml of dichloromethane ($CH_2Cl_2$) at 0° C. and is stirred at this temperature for 30 minutes, then for one hour at room temperature. The solvent is evaporated and a slightly yellow solid is obtained (CgPBr). NMR $^{31}P$ δ 53.5 (in $CH_2Cl_2$):

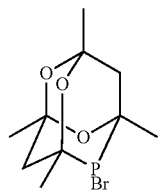

Compound CgPBr

In a second stage, a solution of butyllithium (BuLi) in hexane (1.6 M, 0.01 mol, 6.25 ml) is slowly added to a solution of 1,2-benzene(dimethanol) (2.0725 g, 0.015 mol) in tetrahydrofuran (THF) (50 ml) at 0° C. The mixture is brought slowly to room temperature and stirred for 1 hour. A solution of CgPBr (2.9511 g, 0.01 mol) in THF (50 ml) is then slowly added to the above suspension at 0° C. in 30 minutes and the mixture is stirred for 3 hours at room temperature. The solvent is evaporated, the solid obtained is dissolved in $CH_2Cl_2$ (50 ml) and 50 ml of water is added. The aqueous phase is extracted with 50 ml of $CH_2Cl_2$ and the combined organic phases are dried over $Na_2SO_4$, filtered and the solvent is evaporated. The compound CgP-OH (see formula below) is purified by silica column chromatography using an ethyl acetate/hexane mixture (⅙ by volume) as solvent, under nitrogen pressure.

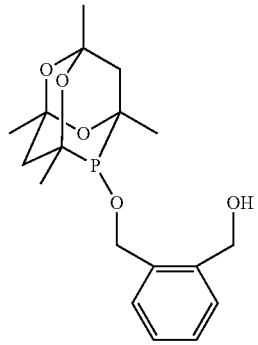

Compound CgP—OH

Amount obtained: 2.89 g (yield 82%)
$^{31}P$ NMR δP 87.9 ($CDCl_3$)
Production of Ligand A
1-Methylpyrrolidin-2-one (0.01 g, 0.1 mmol) is added to a mixture of R-binaphthol (1.00 g, 0.00349 mol) and $PCl_3$ (5 ml) with stirring. The mixture is refluxed for 10 minutes and then, at ambient temperature, all the volatile compounds are evaporated under vacuum. Toluene (20 ml) is added and the solvent is evaporated under vacuum so as to remove the traces of $PCl_3$, and the binaphthol chlorophosphite compound obtained is dried under vacuum (0.067 mbar) for 1 hour. A solution of CgP-OH compound (1.2206 g, 0.03464 mol) and of $NEt_3$ (1 ml, 0.7260 g, 0.00717 mol) in THF (50 ml) is slowly added to a solution of binaphthol chlorophosphite synthesized above, in THF (40 ml) at 0° C., and the mixture is stirred for 3 hours. At ambient temperature, the suspension is then filtered, the cake is washed with THF (2×20 ml) and the solution is evaporated. The compound is purified by silica column chromatography using, as solvent, an ethyl acetate/hexane mixture (1/15 by volume) under nitrogen pressure.

Amount obtained: 1.09 g (yield 47.1%)

$^{31}P$ NMR $\delta P$ 140.6; 140.2 and 86.9; 86.4 ($CD_2Cl_2$)

Production of Ligand B

1-Methylpyrrolidin-2-one (0.01 g, 0.1 mmol) is added to a mixture of biphenol (1.0000 g, 0.00537 mol) and $PCl_3$ (5 ml) with stirring. The mixture is refluxed for 10 minutes and then, at ambient temperature, all the volatile compounds are evaporated under vacuum. Toluene (20 ml) is added and the solvent is evaporated under vacuum so as to remove the traces of $PCl_3$, and the biphenol chlorophosphite compound obtained is dried under vacuum (0.067 mbar) for 1 hour.

A solution of CgP-OH compound (1.7997 g, 0.00510 mol, 95%) and of $NEt_3$ (1.5 ml, 0.0107 mol) in THF (50 ml) is slowly added to a solution of biphenol chlorophosphite, synthesized above, in THF (40 ml) at 0° C., and the mixture is stirred for 3 hours. At ambient temperature, the suspension is then filtered, the cake is washed with THF (2×20 ml) and the solution is evaporated. The compound is purified by silica column chromatography using, as solvent, an ethyl acetate/hexane mixture (1/15 by volume) under nitrogen pressure.

Amount obtained: 2.11 g (yield 72.9%)

$^{31}P$ NMR $\delta P$ 139.0 and 85.9 ($CD_2Cl_2$)

Production of Ligand C

1-Methylpyrrolidin-2-one (0.01 g, 0.1 mmol) is added to a mixture of ortho-cresol (10.8138 g, 0.1 mol) and $PCl_3$ (6.8666 g, 0.05 mol) with stirring. The mixture is refluxed for 10 minutes and then, at ambient temperature, all the volatile compounds are evaporated under vacuum and the residue is distilled under vacuum (0.33 mbar, boiling point 130-135° C.) so as to obtain bis(o-tolyl)chlorophosphite.

A solution of CgP-OH compound (1.5535 g, 0.0044088 mol, 92%) and of $NEt_3$ (1.34 ml, 0.0096 mol) in THF (30 ml) is slowly added to a solution of bis(o-tolyl)chlorophosphite, (1.345 g, 0.00479 mol) in THF (40 ml) at 0° C., and the mixture is stirred for 3 hours. At ambient temperature, the suspension is then filtered, the cake is washed with THF (25 ml) and the solution is evaporated. The compound is purified by silica column chromatography using, as solvent, an ethyl acetate/hexane mixture (1/20 by volume) under nitrogen pressure.

Amount obtained: 1.91 g (yield 72.8%)

$^{31}P$ NMR $\delta P$ 129.4 and 86.3 ($CD_2Cl_2$)

Examples 4 to 12

Hydrocyanation of 3-PN to AdN

The following general procedure is used:

Under an argon atmosphere, a 60-ml tube of Schott type glass equipped with a stopper-septum is charged successively with:

the ligand (0.5 mmol, 2 equivalents in P)

1.21 g (15 mmol, 30 equivalents) of anhydrous 3PN 138 mg (0.5 mmol, 1 equivalent) of $Ni(cod)_2$ Lewis acid (see table for amount)

The mixture is stirred at 70° C. Acetone cyanohydrin is injected into the reaction mixture with a syringe pump at a flow rate of 0.45 ml per hour. After injection for 3 hours, the syringe pump is stopped. The mixture is cooled to room temperature, diluted with acetone and analysed by gas chromatography.

The results are presented in the following table:

TABLE

| Example | ligand | Lewis acid | Lewis acid/Ni (molar) | Linearity | RR (DN) |
|---|---|---|---|---|---|
| 4 | A | $ZnCl_2$ | 1 | 78.1 | 37 |
| 5 | A | $Ph_2BOBPh_2$ | 0.5 | 86.5 | 8.5 |
| 6 | A | TIBAO | 0.5 | 75.7 | 21.5 |
| 7 | B | $ZnCl_2$ | 1 | 79.4 | 31 |
| 8 | B | $Ph_2BOBPh_2$ | 0.5 | 84.7 | 10 |
| 9 | B | TIBAO | 0.5 | 73 | 14 |
| 10 | C | $ZnCl_2$ | 1 | 75 | 30 |
| 11 | C | $Ph_2BOBPh_2$ | 0.5 | 80.9 | 7.2 |
| 12 | C | TIBAO | 0.5 | 73.2 | 24.7 |

The invention claimed is:

1. An organophosphorus compound belonging to the phosphinite-phosphite family, wherein the compound corresponds to formulae (I) or (II):

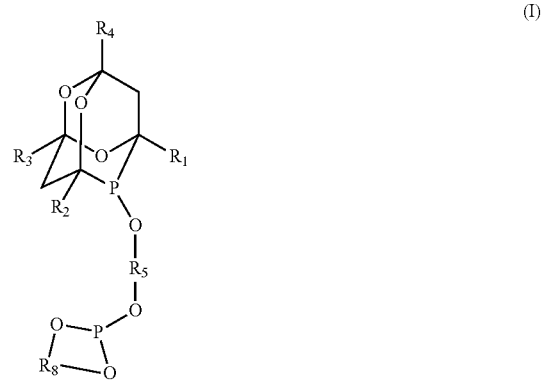

(I)

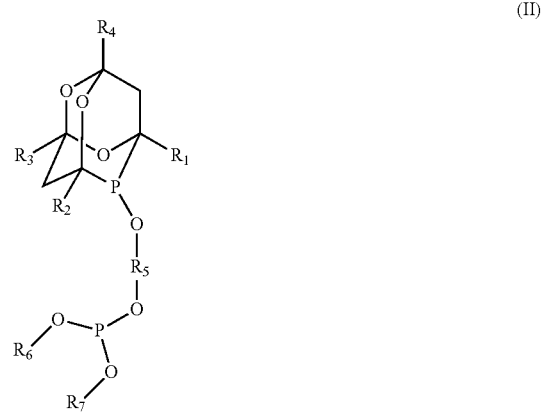

(II)

in which:

$R_1$, $R_2$, $R_3$, $R_4$, $R_6$ and $R_7$, which may can be identical or different, represent a hydrogen atom, a linear or branched alkyl radical having from 1 to 12 carbon atoms which can comprise heteroatoms, a radical comprising a substituted or unsubstituted aromatic or cycloaliphatic ring which can comprise heteroatoms, a carbonyl, alkoxycarbonyl or alkoxy radical, a halogen atom, a nitrile group or a haloalkyl group having 1 to 12 carbon atoms $R_5$ and $R_8$, which can be identical or different, represent a linear or branched aliphatic radical having from 1 to 12 carbon atoms which can comprise heteroatoms, a radical comprising a substituted or unsubstituted aromatic or cycloaliphatic ring which can comprise heteroatoms or several aromatic rings, condensed or joined together.

2. The compound according to claim 1, wherein the compound is selected from the group consisting of the compounds having the following formulae:

Ligand A

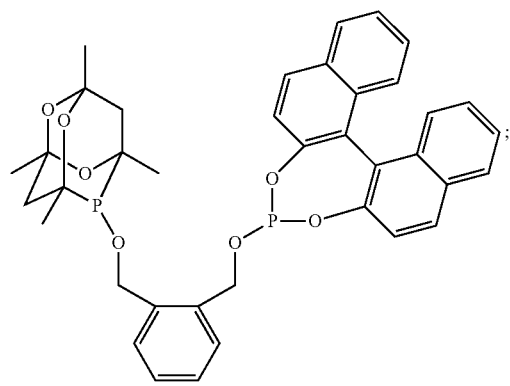

Ligand B

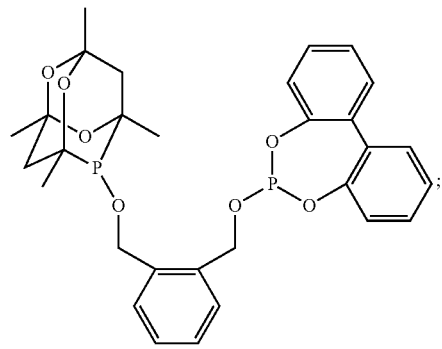

Ligand C

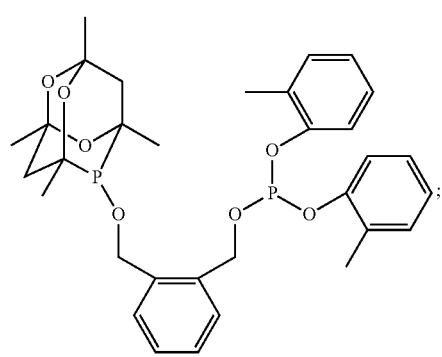

Ligand D

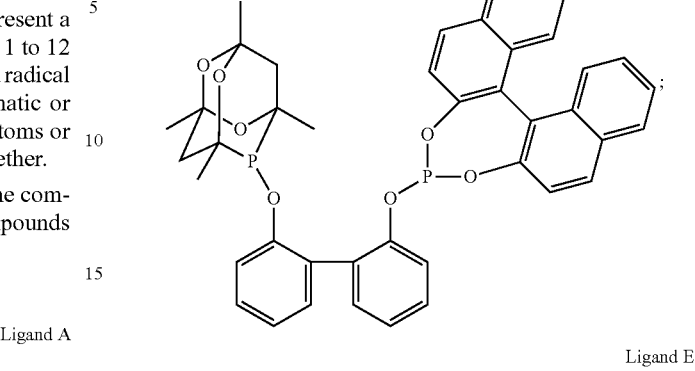

Ligand E

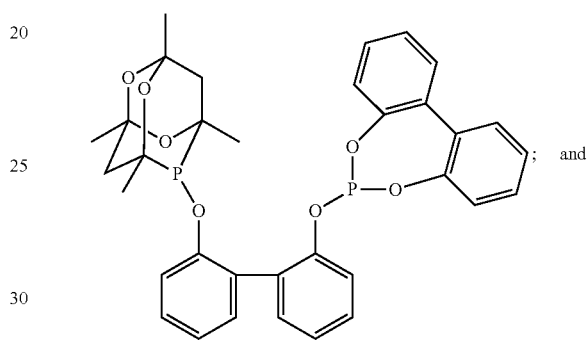

Ligand F

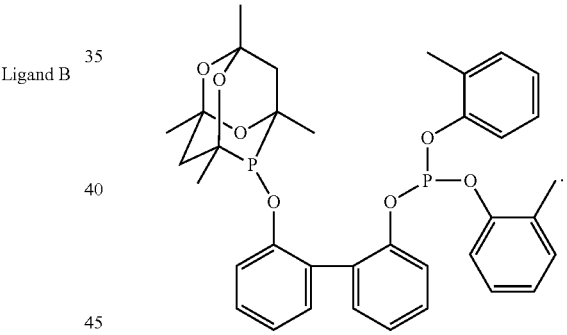

3. A method of preparing a compound according to claim 1, the method comprising reacting a compound obtained by reacting a compound of formula OH—$R_5$—OH with an organo-alkali metal compound with a CgPX compound of formula (1) below where X represents a halogen atom and reacting the resulting compound, with a halogenated organophosphite corresponding to the phosphite residue linked to R5 in general formulae I and II, of formula (2) or (3)

(1)

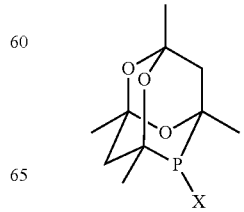

-continued

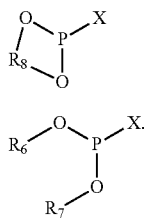

4. The method according to claim 3, wherein the compound obtained by reaction of the compound of formula OH—$R_5$—OH with an organoalkali metal compound is reacted with a CgPX compound of formula (1) in a first stage, and then the product of reaction with the a halogenated organophosphite corresponding to a phosphite residue linked to R5 in formulae I and II, of formula (2) or (3), is reacted in a second stage.

5. A catalytic system comprising a metallic element forming a complex with an organophosphorus compound according to claim 1, wherein the complex corresponds to the following formula (III):

$$M [L_f]_t \quad (III)$$

in which:
M is a transition metal
$L_f$ represents at least one organophosphorus ligand of formula (I) or (II)
t represents a number between 1 and 10 (inclusive).

6. The catalytic system according to claim 5, wherein the metallic element M is selected from the group consisting of nickel, cobalt, iron, ruthenium, rhodium, palladium, osmium, iridium, platinum, copper, silver, gold, zinc, cadmium, and mercury.

7. A method of hydrocyanation of a hydrocarbon compound, the method comprising performing the hydrocyanation of the hydrocarbon compound, wherein the hydrocarbon compound comprises at least one ethylenic unsaturation by reaction in a liquid medium with hydrogen cyanide in the presence of a catalytic system according to claim 5, wherein the metallic element is nickel.

8. The method according to claim 7, wherein the organic compound bearing at least one ethylenic unsaturation is a diolefin selected from the group consisting of butadiene, isoprene, hexadiene-1,5, and cyclooctadiene-1,5, an ethylenically unsaturated aliphatic nitrile, a monoolefin or a mixture of several of these compounds.

9. The method according to claim 7, wherein the amount of nickel compound is selected in such a way that there is, per mol of organic compound that is to undergo hydrocyanation or isomerization, between $10^{-4}$ and 1 mol of nickel or of the other transition metal employed and in that the amount of organophosphorus compounds used is selected in such a way that the number of moles of these compounds relative to 1 mol of transition metal is from 0.5 to 100.

10. The method according to claim 7, wherein the ethylenically unsaturated compound is an ethylenically unsaturated nitrile compound and in that it is carried out in the presence of a catalytic system comprising at least one compound of a transition metal, at least one phosphinite-phosphite of formula (I) or (II) and a cocatalyst comprising at least one Lewis acid.

11. The method according to claim 10, wherein the ethylenically unsaturated nitrile compound is an ethylenically unsaturated aliphatic nitrile comprising a linear pentenenitrile or mixtures thereof.

12. The method according t claim 10, wherein the Lewis acid employed as cocatalyst is a compound of an element selected from the group consisting of group Ib, group IIb, group IIIa, group IIIb, group IVa, group IVb, group Va, group Vb, group VIb, group VIIb and group VIII of the periodic table.

13. The method according to claim 10, wherein the Lewis acid is selected from the group consisting of cobalt chloride, ferrous chloride zinc chloride, zinc bromide, zinc iodide, manganese chloride, manganese bromide, cadmium chloride, cadmium bromide, stannous chloride, stannous bromide, stannous sulphate, stannous tartrate, indium trifluoromethylsulphonate, chloride of rare earth element, bromide of rare earth element, and an organometallic compound or a mixture thereof of Lewis acids.

14. The method according to claim 7, further comprising, when hydrocyanating butadiene, a step of isomerizing methyl-2-butene-3-nitrile, present in the reaction mixture resulting from the hydrocyanation of butadiene, in the absence of hydrogen cyanide, in the presence of a catalyst bearing at least one compound of formula (I) or (II) and at least one compound of a transition metal.

15. The method according to claim 8, wherein the ethylenically unsaturated aliphatic nitrile is a linear pentenenitrile.

16. The method according to claim 15, wherein the linear pentenenitrile is pentene-3-nitrile or pentene-4-nitrile.

17. The method according to claim 8, wherein the monoolefin is selected from the group consisting of styrene, methylstyrene, vinylnaphthalene, cyclohexene, and methylcyclohexene.

18. The method according to claim 11, wherein the linear pentenenitrile is pentene-3-nitrile or pentene-4-nitrile.

19. The method according to claim 13, wherein the rare earth element is selected from the group consisting of lanthanum, cerium, praseodymium, neodymium, samarium, europium, gadolinium, terbium, dysprosium, hafnium, erbium, thallium, ytterbium and lutetium 20. The method according to claim 13, wherein the Lewis acid is cobalt chloride, ferrous chloride, yttrium chloride or an organometallic compound selected from the group consisting of triphenylborane, and titanium isopropylate.

* * * * *